(12) United States Patent
Ho et al.

(10) Patent No.: US 7,237,551 B2
(45) Date of Patent: Jul. 3, 2007

(54) CUSHION FOR A PATIENT INTERFACE (75) Inventors: Peter Chi Fai Ho, Pittsburgh, PA (US); Derrick Andrews, Markleton, PA (US)

(73) Assignee: RIC Investments, LLC., Wilmington, DE (US)

( * ) Notice: Subject to any disclaimer, the term of this patent is extended or adjusted under 35 U.S.C. 154(b) by 0 days.

(21) Appl. No.: 11/312,026

(22) Filed: Dec. 20, 2005

(65) Prior Publication Data

US 2006/0130844 A1    Jun. 22, 2006

Related U.S. Application Data (60) Provisional application No. 60/638,869, filed on Dec. 22, 2004.

(51) Int. Cl.
*A62B 18/02* (2006.01)

(52) U.S. Cl. .................. 128/207.13; 128/206.26; 128/205.25; 128/206.24

(58) Field of Classification Search .......... 128/206.24, 128/202.27, 206.14, 207.11, 207.13, 206.25, 128/203.29, 205.25, 206.12, 206.18, 206.19, 128/206.21, 206.23, 206.27
See application file for complete search history.

(56) References Cited

U.S. PATENT DOCUMENTS

| | | | |
|---|---|---|---|
| 2,641,253 A | 6/1953 | Engelder | |
| 2,706,983 A | 4/1955 | Matheson et al. | |
| 2,881,444 A | 4/1959 | Fresh et al. | |
| 2,882,895 A | 4/1959 | Galeazzi | |
| 3,545,436 A | 12/1970 | Holloway | |
| 4,069,516 A | 1/1978 | Watkins, Jr. | |
| 4,782,832 A | 11/1988 | Trimble et al. | |
| 4,907,584 A | 3/1990 | McGinnis | |
| 5,074,297 A | 12/1991 | Venegas | |
| 5,349,949 A | 9/1994 | Schegerin | |
| 5,540,223 A | 7/1996 | Star et al. | |
| 5,647,357 A | 7/1997 | Barnett et al. | |
| 6,155,253 A | 12/2000 | Gamberini | |
| 6,772,760 B2 | 8/2004 | Frater et al. | |
| 6,986,352 B2 | 1/2006 | Frater et al. | |
| 7,007,696 B2 * | 3/2006 | Palkon et al. .......... | 128/207.13 |
| 7,107,989 B2 | 9/2006 | Frater et al. | |

(Continued)

FOREIGN PATENT DOCUMENTS

JP    11-000397    1/1999

(Continued)

OTHER PUBLICATIONS

Tiara Medical Systems, Inc., "Advantage HUSH Nasal Mask,"?, Tiara Medical Systems, Inc.

(Continued)

*Primary Examiner*—Justine R. Yu
*Assistant Examiner*—Shumaya B. Ali
(74) *Attorney, Agent, or Firm*—Timothy A. Nathan (57) ABSTRACT

A respiratory mask is provided having an outer shell coupled to a cushion for the delivery of a gas to a user. The cushion of the respiratory mask has a pleat and varied wall thicknesses about the device in order to provide varying degrees of flexibility and support about the cushion.

10 Claims, 13 Drawing Sheets

U.S. PATENT DOCUMENTS

2003/0019495 A1  1/2003  Palkon et al.
2004/0112385 A1  6/2004  Drew et al.
2004/0144386 A1  7/2004  Frater et al.

FOREIGN PATENT DOCUMENTS

| WO | WO 01/62326    | 8/2001 |
| WO | WO 2004/022146 | 3/2004 |
| WO | WO 2005/021075 | 3/2005 |
| WO | WO 2006/014630 | 2/2006 |
| WO | WO 2006/074513 | 7/2006 |

OTHER PUBLICATIONS

English translation of Japanese publication No. 11-000397.

* cited by examiner

CUSHION FOR A PATIENT INTERFACE

CROSS-REFERENCE TO RELATED APPLICATIONS

This application claims priority under 35 U.S.C. § 119(e) from provisional U.S. patent application No. 60/638,869 filed Dec. 22, 2004 the contents of which are incorporated herein by reference.

BACKGROUND OF THE INVENTION

1. Field of the Invention

The present invention pertains to a respiratory patient interface used to deliver gas to a user. In particular, the present invention is related to a respiratory patient interface having a cushion with a pleat.

2. Description of the Related Art

Obstructive sleep apnea or OSA, obstructive sleep hypopnea, and upper airway resistance syndrome (UARS) are among a variety of known disorders characterized by episodes of complete or partial upper airway obstruction during a state of diminished consciousness, such as sleep, anesthetization, or post anesthesia. OSA, hypopnea, and UARS cause intermittent interruption of ventilation during sleep with the consequence of potentially severe oxyhemoglobin desaturation. Typically, those afflicted with OSA, hypopnea, and UARS experience repeated, frequent arousal from sleep in response to the oxygen deprivation. The arousals result in sleep fragmentation and poor sleep continuity.

Consequences of OSA, hypopnea, and UARS may include debilitating daytime sleepiness and cognitive dysfunction, systemic hypertension, cardiac dysrythmias, pulmonary artery hypertension and congestive heart failure. Other consequences may include a predisposition to myocardial infarction, angina pectoris, stroke, right ventricular dysfunction with cor pulmonale, carbon dioxide retention during wakefulness as well as during sleep, and continuous, reduced arterial oxygen tension. Moreover, the cognitive impairment resulting from OSA, hypopnea, and UARS puts those afflicted at elevated risk of accidents.

The pathogenesis of the airway obstruction that characterizes OSA, hypopnea, and UARS can include both anatomic and functional abnormalities of the upper airway that result in increased air flow resistance. Such abnormalities may include narrowing of the upper airway due to suction forces created during inspiration, the effect of gravity pulling the tongue back to appose the pharyngeal wall, and insufficient muscle tone in the upper airway dilator muscles, among others. It is also believed that excessive soft tissue in the anterior and lateral neck, as commonly observed in obese persons, can apply sufficient pressure to internal structures to narrow the upper airway and restrict air flow.

Conventional treatment of OSA, hypopnea, and UARS has included surgical intervention, such as uvalopalotopharyngoplasty, gastric surgery for obesity, mandibular advancement procedures, maxillo-facial reconstruction, and tracheostomy. However, surgery potentially involves considerable risk of post-operative morbidity and mortality. In addition, the failure rate of surgery is disturbingly high. Pharmacological therapy has also been proposed to treat OSA, hypopnea, and UARS; however, results have been generally disappointing.

More recently, continuous positive airway pressure (CPAP) or bi-level positive airway pressure applied during sleep has been used to treat OSA, hypopnea, and UARS patients. Positive pressure is applied in the upper airway to splint or support the airway open, thereby preventing its collapse and the resultant airway obstruction. A typical positive airway pressure device comprises a flow generator (e.g., a blower) that delivers gas via a delivery conduit to a patient interface, such as a mask. It is also known to deliver the positive airway pressure therapy as a continuous positive airway pressure (CPAP), a variable airway pressure, such as a bi-level pressure that varies with the patient's respiratory cycle (Bi-PAP), or an auto-titrating pressure that varies with the monitored condition of the patient. Pressure support therapies are also provided to treat other medical and respiratory disorders, such as Cheynes-Stokes respiration, congestive heart failure, and stroke.

Many patient interfaces are well known in the art. For instance, masks which provide a seal between the compressed air and the patient are common. These interfaces include nasal pillows with prongs which fit into the nares of the patient, nasal masks which fit over the patient's nose, nasal-oral masks that fit over the mouth and nose, and full face masks which fit over the patient's entire face. For such devices to be effective, two competing goals need to be balanced: comfort and support. Comfort may be enhanced by reducing the area of contact between the mask and the patient; or use of a soft, lightweight, flexible material. If the mask proves to be uncomfortable, patient compliance will be low. In contrast, to enhance the ability of the mask to support its weight and associated hoses and attachments, the mask should ideally be constructed from a rigid material and have a large contact area between the mask and the patient.

One mask which attempts to balance the competing goals of comfort and support is disclosed in U.S. Pat. No. 4,907,584. This mask has a rigid support portion and a cushion. The cushion includes a flexible flap to form a seal between the patient and the mask. In order for the flap to operate effectively, the flap must be sufficiently rigid to support the mask and sufficiently flexible to be comfortable. Although the '584 patent has substantially advanced the art, it could still be further improved upon. For instance, since the flap is required to balance between comfort and support, the resulting design must compromise between these two goals.

Other patient interfaces have been suggested which have separate structural features to address the competing goals of support and comfort. For instance, U.S. Patent Application Publication No. 2004/0112385 discloses a mask having a rigid support attached to a cushion. The cushion disclosed in the application includes a double flap. The outer flap contacts the face of the patient and is formed to be flexible in order to provide a comfortable seal. The inner flap is formed to provide support to the cushion either alone or in combination with the outer flap.

This device advances the art by separating the two competing goals of comfort and support into separate structural elements. By so doing, this allows each of these features to be customized to achieve their separate purpose rather than having a single structural element which attempts to balance these two competing goals. Yet, even this design presents several drawbacks. One major drawback to this design is that it assumes the forces exerted on the mask are consistent about its circumference. In reality, the region about a patient's mouth and/or nose has a complex geometry requiring differing amounts of flexibility and support to achieve an adequate seal and differing amounts of rigidity to provide adequate support. Secondly, forming a cushion with an internal flap has proved difficult to manufacture and has resulted in rejects and wasted material. Typically, these masks are manufactured by an injection molding process. One drawback to this manufacturing method is that it is difficult to flow material into thin walls and undercuts as is needed to form this type of cushion.

To overcome these disadvantages, other masks have been suggested to provide a separate structure to seal the mask and a separate structure to provide support while simplifying the manufacturing process. One such mask is disclosed in U.S. Pat. No. 5,349,949. The mask disclosed in this patent has a rigid shell provided with fastening straps to hold the mask on the user's head. Connected to the shell is a face cover constructed from an elastomeric material. The face cover contacts the user's face along an internal lip. Adjacent to the lip is a deformable fold with resilient spring-like elements. One advantage this device has over the device disclosed in the previous publication is that it removes the thin walls and undercuts while separating the structure used to provide a seal from the structure used to provide support to the face cover. Yet, even this device has several drawbacks. For instance, the deformable fold has a consistence shape about the circumference of the face cover. Therefore, it is incapable of providing differing support and flexibility as needed about the user's face.

Accordingly, it would be desirable to have a respiratory mask that is configured to deliver a gas to a patient. It would also be desirable to have a respiratory mask that provides separate structural elements to provide support and flexibility to the respiratory mask. It would be further desirable to have a respiratory mask which is capable of providing differing support and flexibility in different regions of the mask. It would still be further desirable to have a respiratory mask that is capable of providing the above noted features while being constructed in a manner that simplifies the manufacturing process.

SUMMARY OF THE INVENTION

In accordance with the broad teachings of the invention, a cushion for a respiratory mask having a shell and a cushion is disclosed. The cushion includes three portions: a flap portion, a middle portion, and a connection portion. The connection portion is adapted to couple with the shell of the respiratory mask. The middle portion provides moderate support and flexibility. The flap portion is configured to provide a comfortable seal with the user's face by providing more flexibility. The cushion further includes a pleat about a portion of the cushion to provide a localized region of flexibility for forces exerted in an axial direction toward or away from the user's face. The pleat also provides some additional rigidity for forces which are exerted in a direction other than axially.

In another aspect, the invention includes a cushion for a respiratory mask having a coupling and a nasal pillow. The nasal pillow includes a hollow body in communication with at least one nare element. The nare element has an opening to permit fluid communication between a patient and the coupling via the hollow body. The nare element further includes a pleat about a portion of the nare element to provide a region of localized flexibility.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
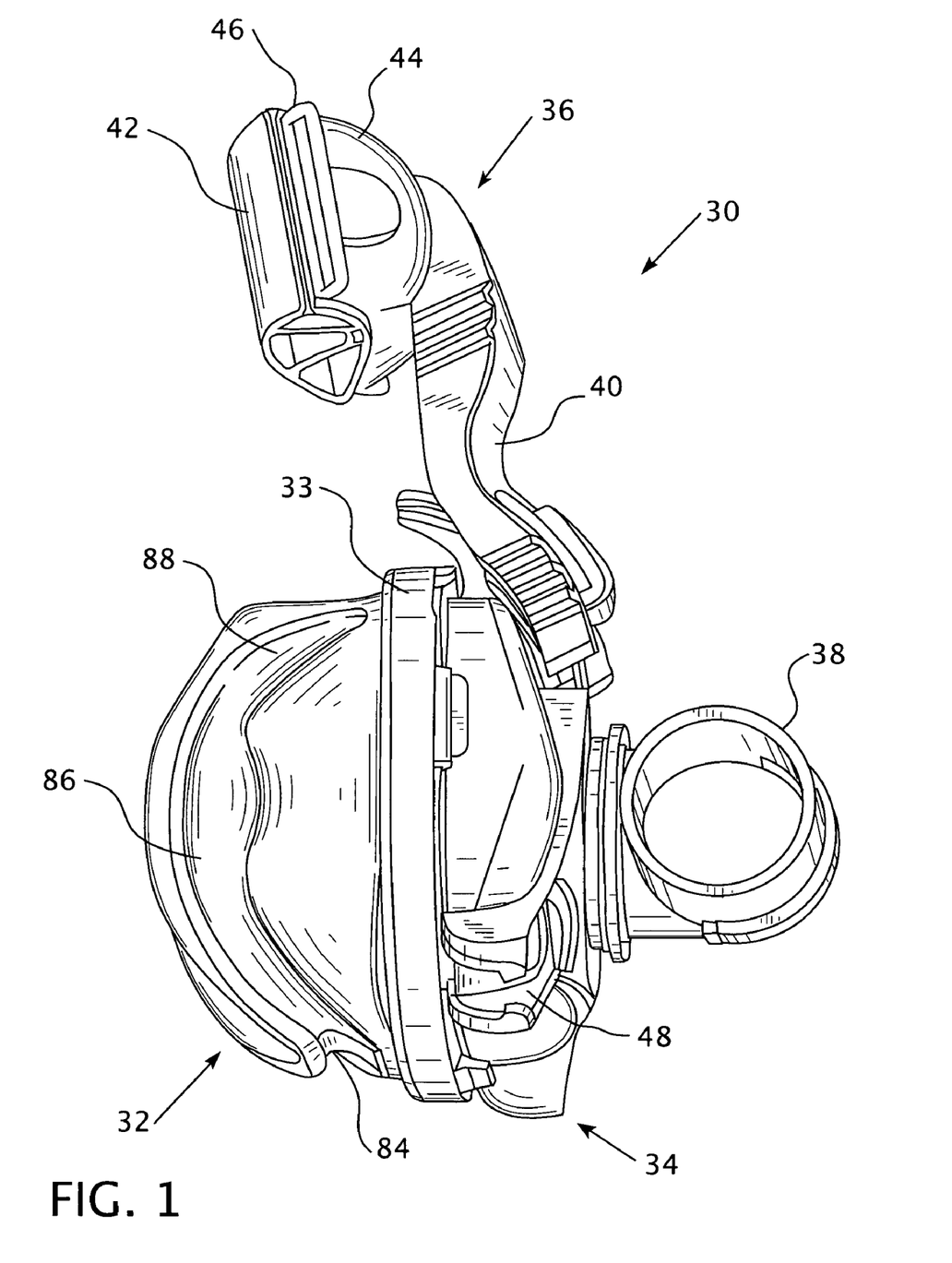
FIG. 1 is a side elevational view of the respiratory mask of the present invention.

FIG. 1 schematically illustrates an exemplary embodiment of a patient interface 30 having a cushion 32 attached to a shell 34 by a capture ring 33. The capture ring fits about cushion 32 and connects to shell 34 to capture a portion of cushion 32 between capture ring 33 and shell 34. Cushion 32 may be attached to shell 34 in a variety of other methods known in the art. For instance, the cushion could be attached via an adhesive to the shell. Alternatively, the cushion could be attached by overmolding the cushion onto the shell. Of course, other methods of interconnecting the shell to the cushion may be contemplated without departing from the scope of the present invention.

The patient interface also includes a forehead support 36 and a coupling 38 connected to the shell 34. A conduit 35 is connected to the patient interface 30 via coupling 38. The conduit delivers pressurized gas produced by a positive pressure device 37 to the patient interface. The positive pressure device may create pressurized gas in any of a number of commonly known methods such as continuous positive pressure, variable pressure (such as a bi-level pressure that varies with the patient's respiratory cycle), or an auto-titrating pressure that varies with the monitored condition of the patient.

As seen in FIG. 1, forehead support 36 has a frame 40 that extends away from shell 34. The frame is attached to the shell at one end and supports a pad 42 at the other end. Between pad 42 and frame 40 there is a rigid base 44. The respiratory mask is held in place on a user's face by headgear, not shown. The headgear is connected to the forehead support by ears 46 extending from base 44. Similarly, shell 34 has slots 48 adapted to receive pivot members, not shown, which are connected to the headgear. Together, ears 46 and slots 48 secure the headgear to the respiratory mask. The pad is flexible so that it can conform to the particular shape of the user's forehead.

Figure 2:
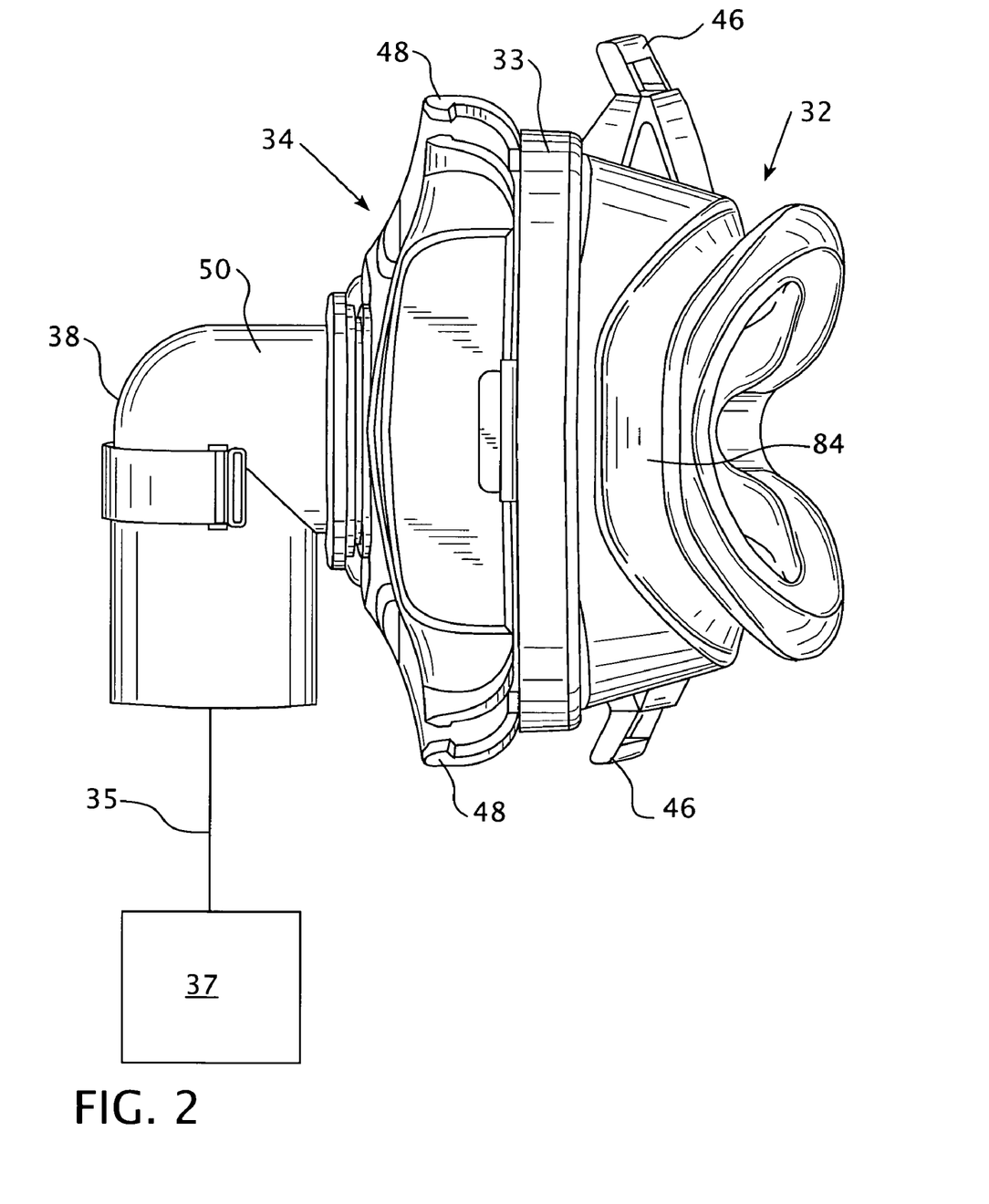
FIG. 2 is a bottom plan view of the respiratory mask and a schismatic of a conduit and a positive airway pressure device.

As seen in FIG. 2, coupling 38 is an elbow connector 50 that is directed substantially coplanar with shell 34 so that the attached conduit does not extend directly perpendicular from shell 34. One of ordinary skill in the art can best appreciate that having a conduit which extends perpendicularly from the respiratory mask would place increased pressure on the mask resulting in discomfort. In addition, having a conduit extending outward from the patient interface in this fashion may also prove to be unwieldy. Elbow connector 50 is pivotably connected to shell 34 so that as the user moves about the conduit may also freely move. Otherwise, as the user moves, the conduit could exert forces on the patient interface which could result in discomfort to the user or even compromise the seal created between cushion 32 and the user's face.

As seen in FIGS. 3A, 3B, 4A, and 4B, cushion 32 has a generally triangular-shaped periphery and fits over the user's nose. However, it is well known in the art that various patient interfaces can be constructed which cover the user's nose and mouth (nasal-oral), cover a majority of the user's face (full-face mask), or fit within the user's nares. The present invention contemplates that the unique aspects of this invention could be utilized on a variety of different patient interfaces without departing from the scope of this invention. Cushion 32 is configured to provide a flexible seal between the user and the shell. In order to be effective, cushion 32 should be comfortable. Otherwise patient compliance would be reduced. In addition, cushion 32 should also provide a substantially hermetic seal between the user and the shell. The effectiveness of the cushion and the entire respiratory mask would be compromised if this seal is not maintained.

Cushion 32 has a flap portion 52, a middle portion 54, and a connection portion 56. Each portion is specifically configured to achieve different goals. Flap portion 52 is configured to provide a secure seal between the user and the shell. The middle portion is configured to provide support to the cushion to resist the forces exerted upon the cushion. The connection portion is designed to provide a secure connection between the cushion and the shell.

Each portion of the cushion has an apex region, a pair of side regions, and a bottom region. For instance, the flap portion has an apex flap 58 adjacent a pair of side flaps 60. The side flaps are joined by bottom flap 62 to form a substantially triangular-shaped flap portion. The middle portion is adjacent to the flap portion. Middle portion 54 has a middle apex region 64 adjacent a pair of middle side regions 66. The middle side regions are joined together by a middle bottom region 68. Lastly, the connection portion has an apex connection region 70 adjacent a pair of connection side regions 72. The side regions 72 are adjacent connection bottom region 74. Connection portion 56 has a collar 76 which may be captured between shell 34 and capture ring 33 to form a substantially hermetic seal with shell 34. Extending from collar 76 is a pair of alignment projections 78 and alignment slots 80. Together alignment projections 78 and alignment slots 80 act to prevent cushion 32 from being misaligned relative to shell 34.

Figure 3A:
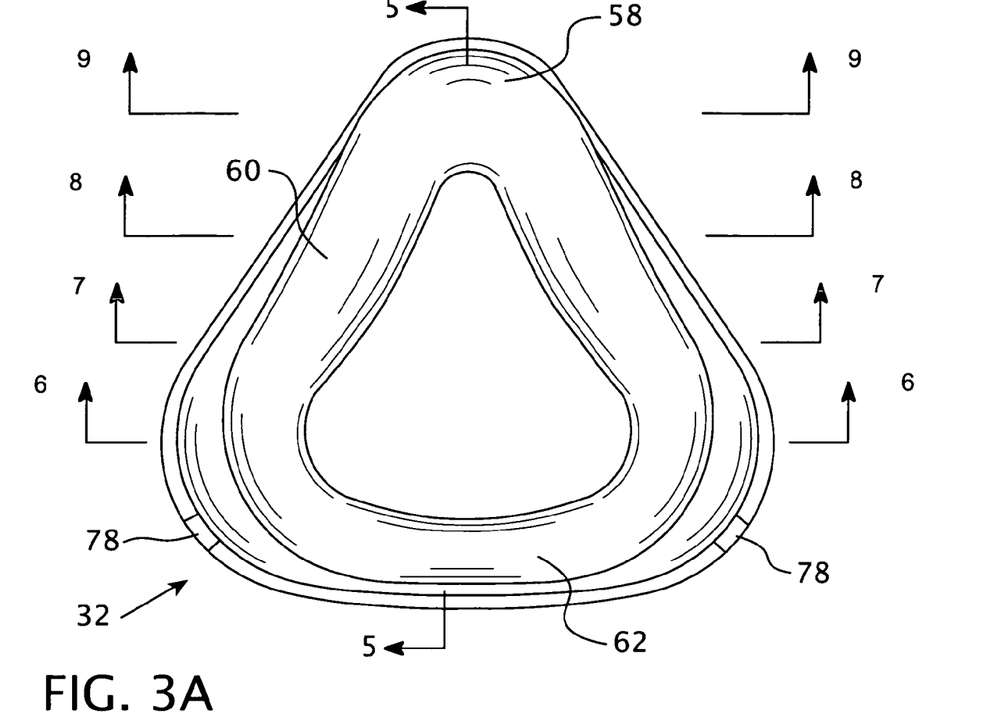
FIG. 3A is a front elevational view of a cushion of the respiratory mask.
Figure 3B:
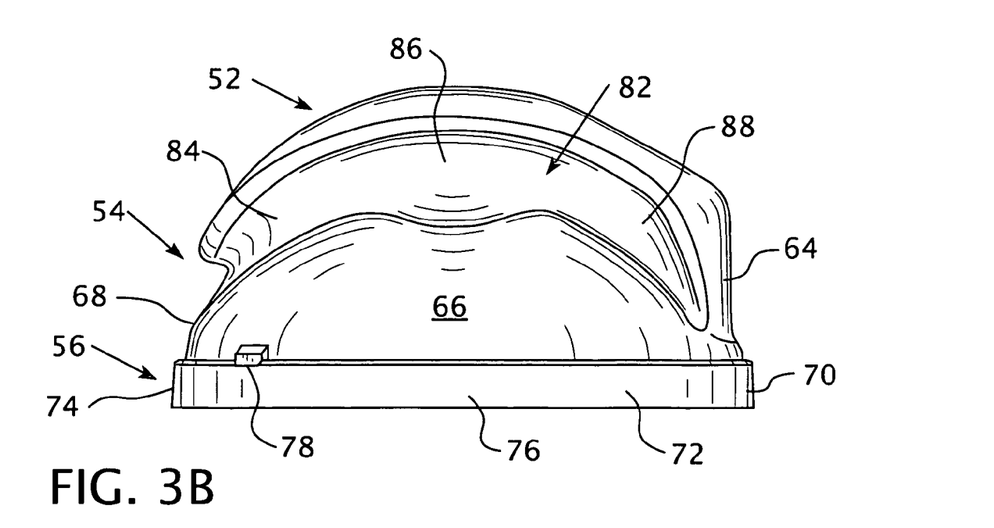
FIG. 3B is a side elevational view of the cushion.
Figure 4A:
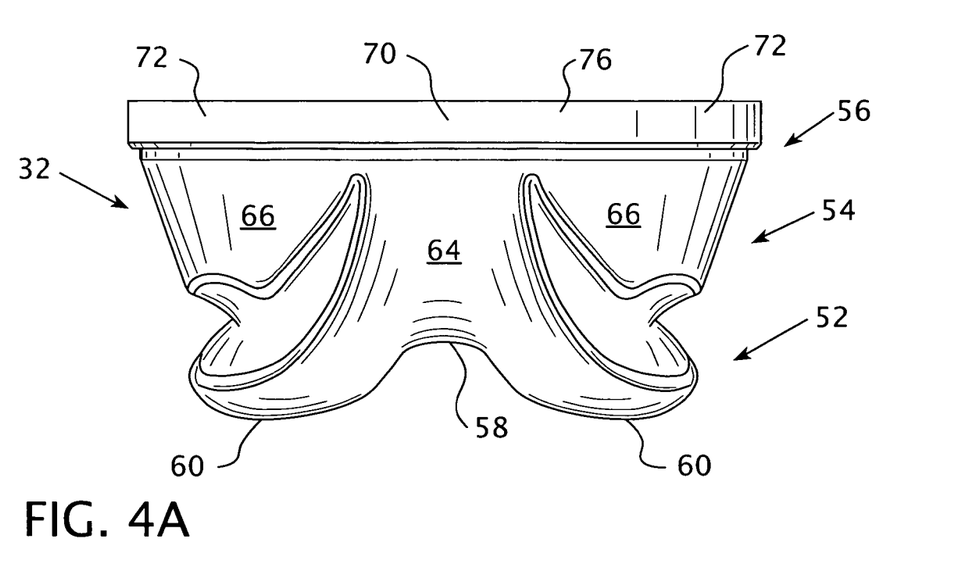
FIG. 4A is a top plan view of the cushion.
Figure 4B:
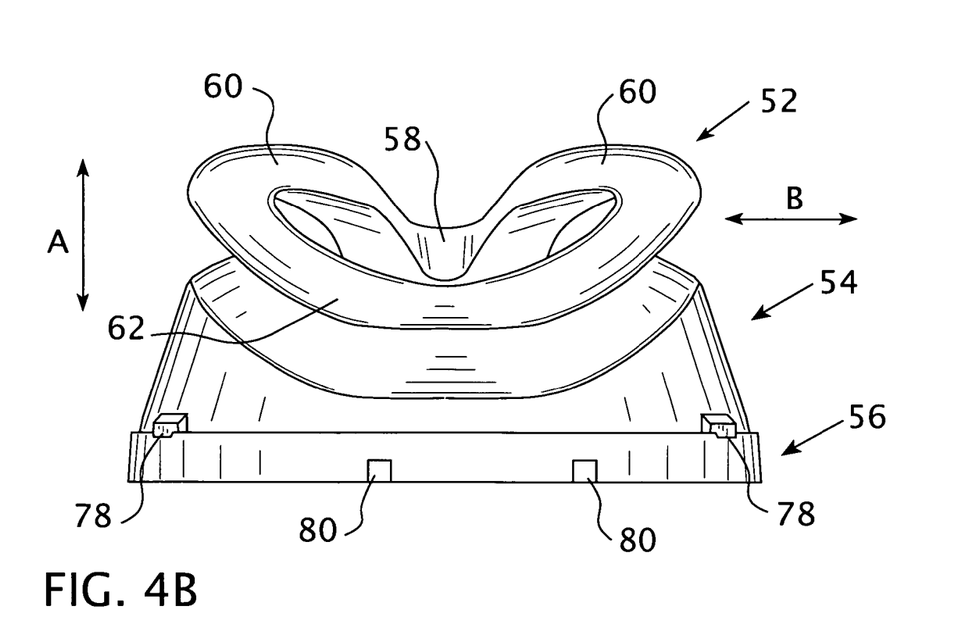
FIG. 4B is a bottom plan view of the cushion.

Another aspect of this exemplary embodiment of the present invention is the incorporation of a pleat 82 as best appreciated with reference to FIGS. 3B and 4B. The pleat extends about a portion of the cushion. The pleat provides an integral corrugation which provides a spring-type action perpendicular to the pleat as indicated by double arrow A. In combination with the varied wall thickness, this feature allows the spring to become progressively stiffer as it is compressed. This is accomplished at least in part by having the pleat located adjacent the flap and extending inwardly. As pressure is applied to the flap, it will ultimately abut against the pleat and become more rigid. In the event that multiple pleats are used, this feature can provide progressively increasing resistance as the pressure is increased. Therefore, at the option of the user, the amount of resistance provided by cushion may be varied.

The use of pleats also simultaneously makes the cushion more rigid in the off-axis direction indicated by double arrow B. This allows the cushion to resist radial forces applied parallel to the pleat. The depth of pleat 82 may be deepened to provide a more elastic region or the number of pleats could be increased to further enhance these effects. In other regions, pleat 82 may be comparatively shallow or completely removed from some regions to reduce this effect.

Pleat 82 has a bottom pleat 84 which extends around the mid bottom region 68 and a pair of side pleats 86 which extend up the mid side regions 66. Finally, pleat 82 turns towards the connection portion 56 and terminates with a pair of apex pleats 88. Apex pleats 88 are not interconnected. Instead, apex pleats 88 terminate short of each other. Pleat 82 extends about the cushion proximate the flap portion which allows the pleat to be more responsive to forces exerted in this region of the cushion. Namely, pleat 82 is more responsive to forces exerted on the flap by the user's face in direction A than by forces exerted radially inwardly on cushion in the direction indicated by arrow B. Alternatively, the pleat could be located in other regions of the cushion to be more responsive to the forces exerted in these other regions of the cushion.

One of ordinary skill in the art can best appreciate that pleat 82 may vary in the distance that it deviates. The pleat is shown extending inwardly; however, the pleat could also extend radially outwardly without departing from the teachings of the present invention. However, it is presently contemplated that having the pleat extend inwardly is preferable so that the overall size of the cushion is reduced. Moreover, having the pleat extend inwardly minimizes the possibility that external items could be pinched within the pleat. The height of the pleat may also be varied to adjust the strength provided by the pleat.

As shown in the exemplary embodiment, the pleat has a generally smoothly curved configuration. However, the term "pleat" as used herein should be broadly interpreted to include any feature which deviates from a substantially planar region surrounding the pleat. For instance, the present invention also contemplates that the pleat may have a variety of cross-sectional configurations including a smoothly curved cross-section or creased into a jagged saw-tooth or rectangular cross-section. As shown in the first exemplary embodiment, the pleat is shown as a single pleat. However, the present invention also contemplates that multiple pleats may be placed adjacent to one another to multiply the advantages provided by the pleat.

Figure 5:
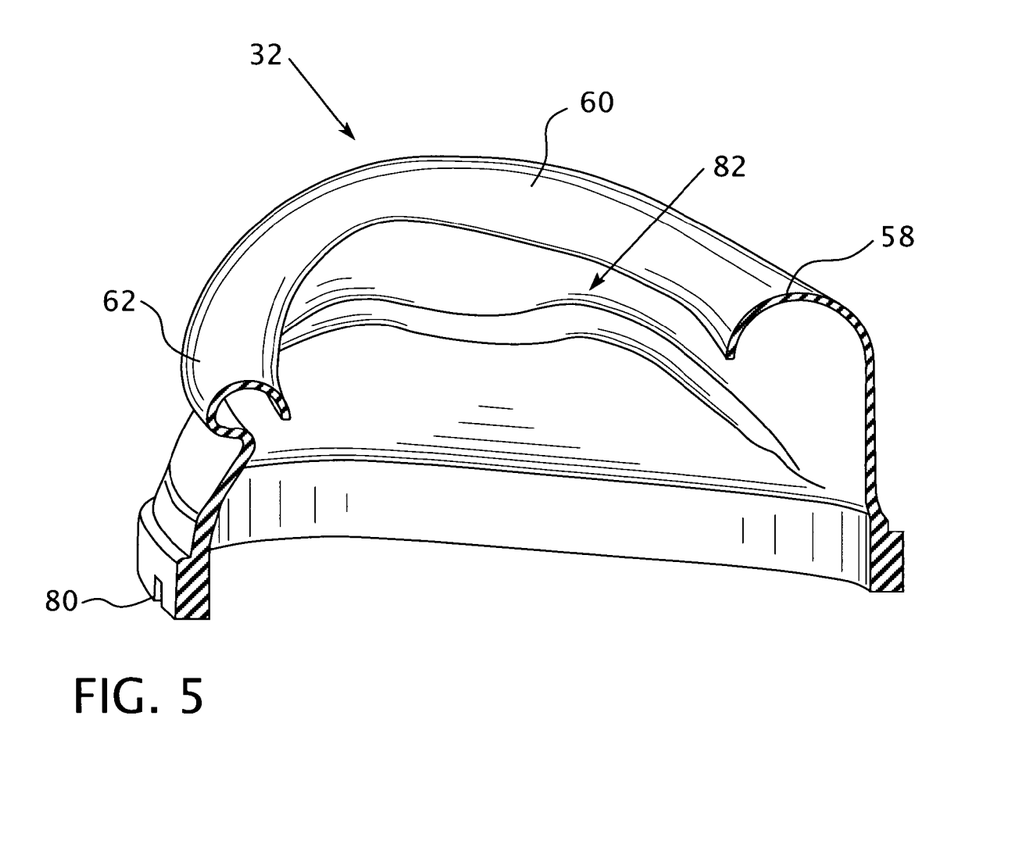
FIG. 5 is a side cross-sectional view of the cushion along line 5-5 of FIG. 3.
Figure 6:
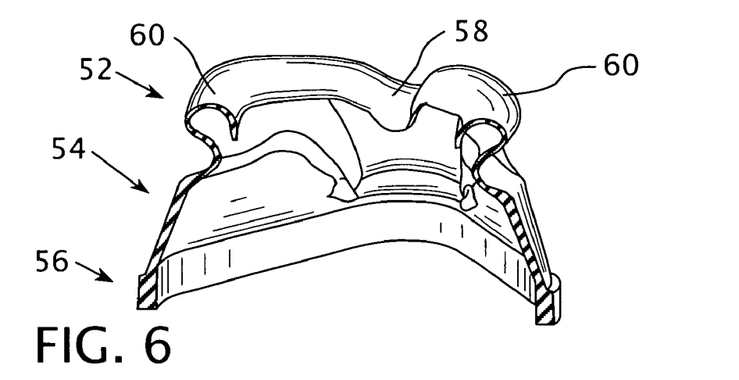
FIG. 6 is a cross-sectional view of the cushion along line 6-6 of FIG. 3.
Figure 7:
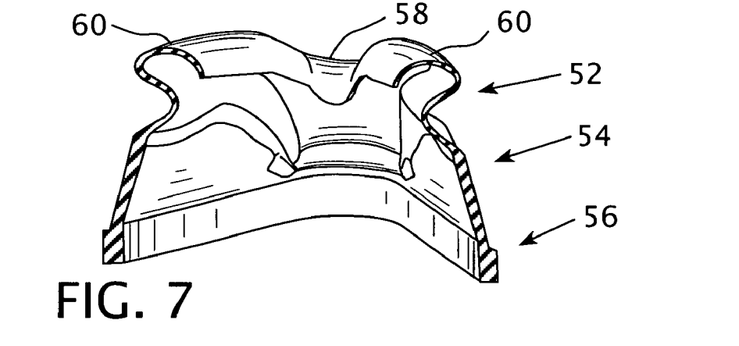
FIG. 7 is a cross-sectional view of the cushion along line 7-7 of FIG. 3.
Figure 8:
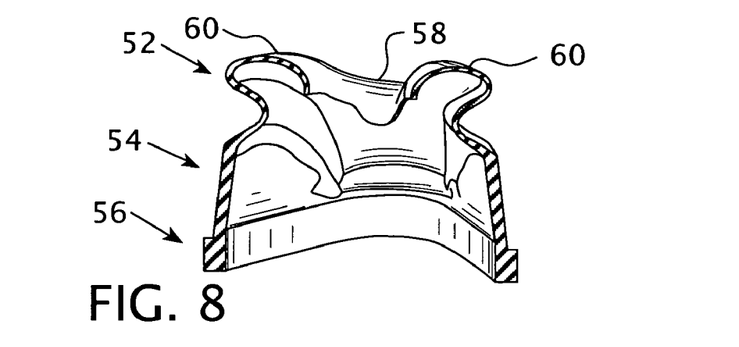
FIG. 8 is a cross-sectional view of the cushion along line 8-8 of FIG. 3.
Figure 9:
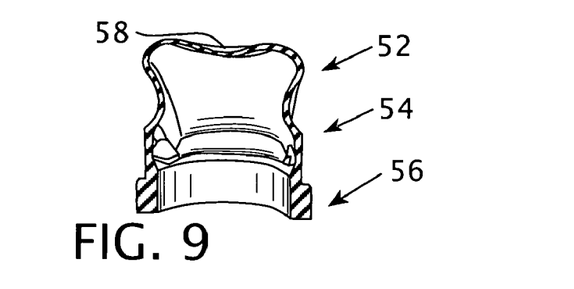
FIG. 9 is a cross-sectional view of the cushion along line 9-9 of FIG. 3.

As seen in FIGS. 5 and 8, the apex flap, side flaps, and bottom flap have lengths which vary between each region. Looking at the cross-section, it can be best appreciated that the flaps extend away from the middle portion in a cantilevered manner. By altering the length of the flaps, the moment of inertia can be varied in different regions. For example, apex flap 58 may have a comparatively long length compared to bottom flap 62 with side flaps 60 having a length which transitions between the two. Providing apex flap 58 with a longer length permits this flap to be comparatively more deformable so that it can properly seal against the rapidly changing geometry about the bridge of the user's nose. In contrast, bottom flap 62 is comparatively shorter. In this region of the user's face, the geometry of the user's face changes very slowly. Therefore, it is not necessary to have as deformable a flap as is needed in the apex region. Instead more support is needed in this region. Therefore, a flap with a shorter length is utilized.

With reference to FIGS. 6-9, the cross-sectional thickness of flap portion 52, middle portion 54, and connection portion 56 may be seen. Generally, the wall thickness of each portion varies with the connection portion 56 being relatively thick. The middle portion has a generally moderate wall thickness, and the flap portion has a relatively thin wall thickness. The wall thickness of connection portion 56 is relative thick in order to provide a secure interface with shell 34. The middle portion has a moderate wall thickness in order to provide adequate strength without wasting material. Finally, flap region has a comparatively thin wall thickness so that it may easily conform to the particular shape of the user's face. Otherwise, cushion 32 may not properly fit and result in discomfort or poor sealing. Of course, one skilled in the art can best appreciate that the wall thickness of these regions could be varied without departing from the teachings of the present invention.

Figure 10A:
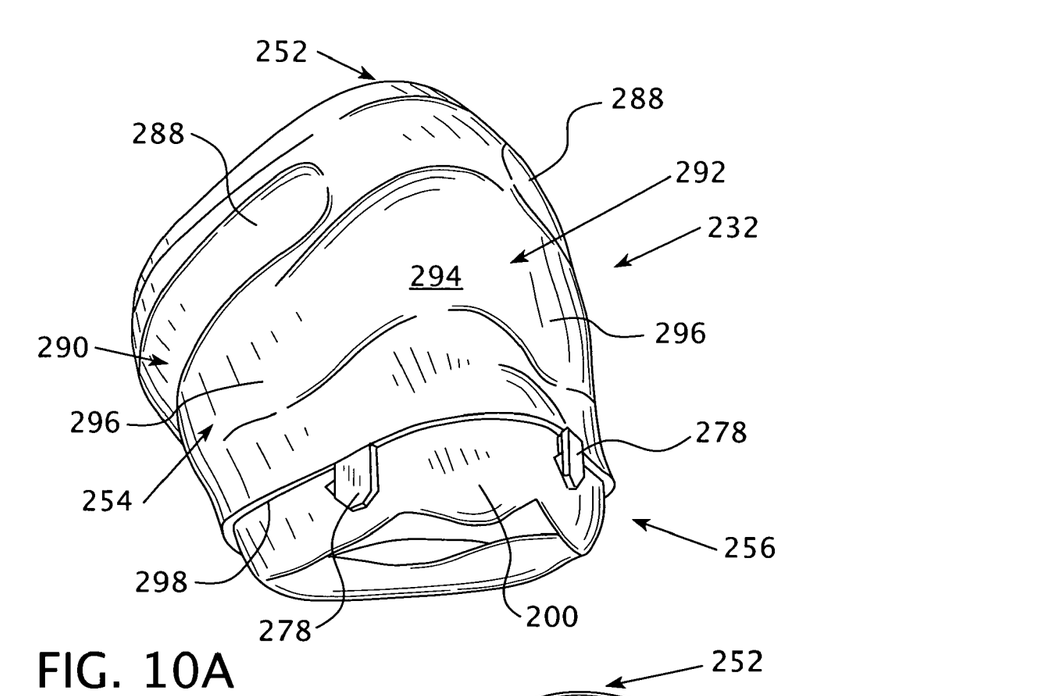
FIG. 10A is a top perspective view of an alternative embodiment of the cushion.
Figure 10B:
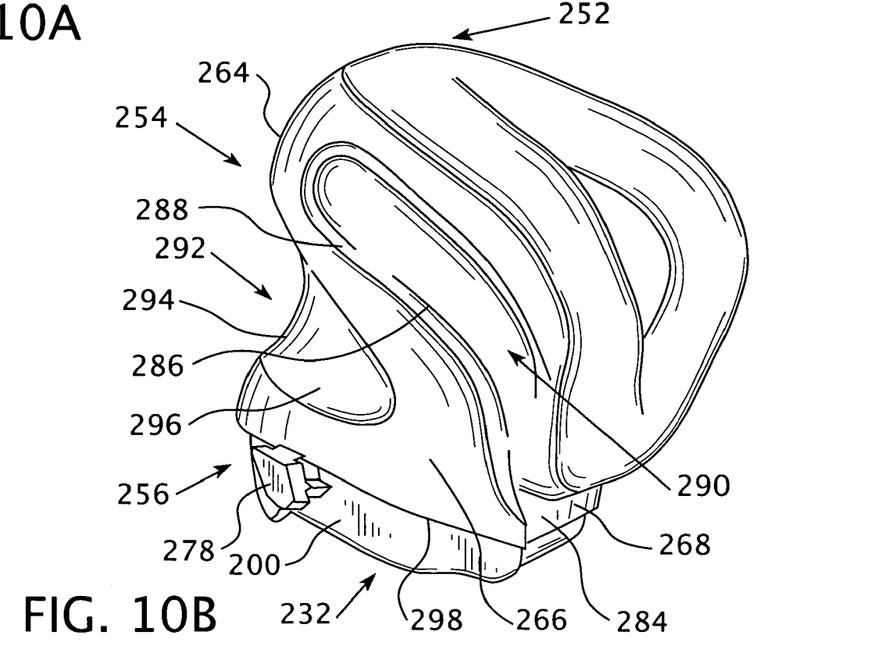
FIG. 10B is a bottom perspective view of a first alternative embodiment of the cushion.
Figure 11:
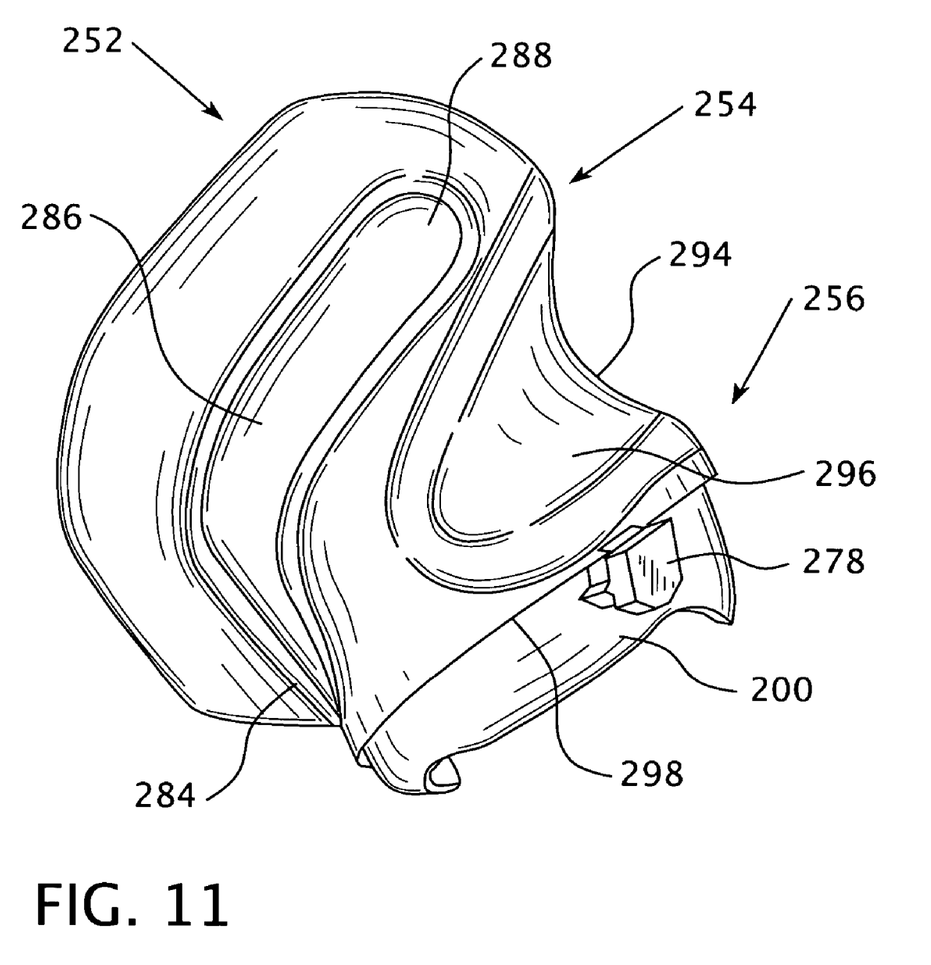
FIG. 11 is a side elevational view of a first alternative embodiment of the cushion.
Figure 12:
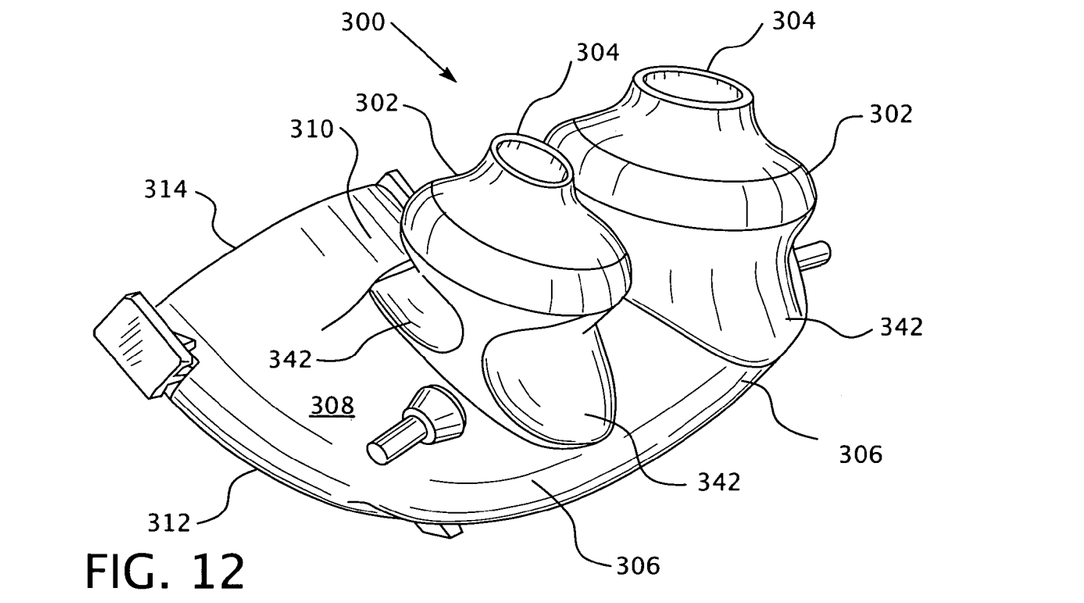
FIG. 12 is a front perspective view of a second alternative embodiment of the cushion.

In a second exemplary embodiment of the present invention, cushion 232 is shown in FIGS. 10A and 10B as a nasal mask covering the user's nose. Once again, cushion 232 has a flap portion 252, a middle portion 254, and a connection portion 256. Cushion 232 has a first pleat 290 that extends about a portion of the cushion and a second pleat 292 which extends about another portion of the cushion. First pleat 290 includes a bottom pleat 284, a pair of side pleats 286, and a pair of apex pleats 288.

Similarly, the second pleat 292 has an apex pleat 294 and a pair of side pleats 296. Second pleat 292 is shallower than first pleat 290. Accordingly, second pleat 292 is substantially more rigid than first pleat 290 and thus more capable of resisting axially directed forces than first pleat 290. However, second pleat 292 is less rigid in the axial direction than if this region did not have a pleat at all.

The first pleat extends about middle portion 254 and proximate flap portion 252. One can appreciate that the strength modifications this pleat provides will be more responsive to forces exerted on the flap portion than forces exerted on the connection portion. In contrast, the second pleat extends about middle portion 254 and proximate connection portion 256. The second pleat will be more responsive to forces exerted on the connection portion than the flap portion. Together the first pleat 290 and second pleat 292 exhibit one embodiment of the present invention utilizing the unique strength modifying characteristics of present invention. The first pleat is more responsive to forces applied to flap portion 252 and provides a region on increased flexibility about the mid bottom region and the mid side regions of flap portion 252. This creates a hinging motion relative to the mid apex region of the cushion proximate flap portion 252. The second pleat is more responsive to forces exerted on connection portion 256 and provides a region of increased flexibility about the mid top region and mid side regions of the connection portion. This creates a hinging motion relative to the mid bottom region of the cushion proximate the connecting portion.

The connection portion of this exemplary embodiment also includes an alignment projection 278. Unlike the prior embodiment, connection portion 256 is formed having a shoulder 298 about step 200. However, the unique features of this invention can be utilized in a variety of masks with differing connection features. The cushion is coupled to a shell, not shown. One unique feature of this embodiment is that by strategic placement of pleats 290 and 292, this cushion provides a hinge-like action. With reference to FIG. 10B, pleats 290 and 292 form a pair of integral hinges generally opposed to one another. Pleat 292 allows the middle apex region 264 and middle side regions 266 to flex easier than middle bottom region 268. Often with such cushions a conduit may extend outward at a variety of different angles. The second pleat permits the cushion to easily adapt as the angle between the cushion and conduit changes. Pleat 290 allows middle side regions 266 and middle bottom region 268 to flex together easier than middle apex region 264. Pleat 290 acts in a similar manner as pleat 82 in the previous embodiment which is more responsive to forces applied to the flap portion.

Cushion 232 may be formed with any of a variety of methods commonly known in the art. Preferably, cushion 232 is formed by an injection molding process. The pleats provide an integral secondary flap without the need to form an undercut as is necessary in cushions which utilize an internal secondary flap. Cushion 232 may be formed from any suitable material. Preferably, the cushion is manufactured from an elastic material such as silicone. Of course, a variety of other materials may be utilized without departing from the present invention.

Another embodiment of the invention is shown in FIGS. 12-16 in which the unique aspects of the present invention are incorporated into a nasal pillow 300. An exemplary nasal pillow is fully disclosed in U.S. patent application Ser. No. 10/918,832, the contents of which are hereby incorporated by reference herein. The nasal pillow 300 of the present invention includes nare elements 302 terminating at an opening 304. Nare elements 302 are joined together by outlet legs 306 that merge together into body 308. Body 308 has an inner curved surface 310 and an outer curved surface 312 defining an internal cavity 313 therebetween. Body 308 terminates at an opening 314.

Figure 13:
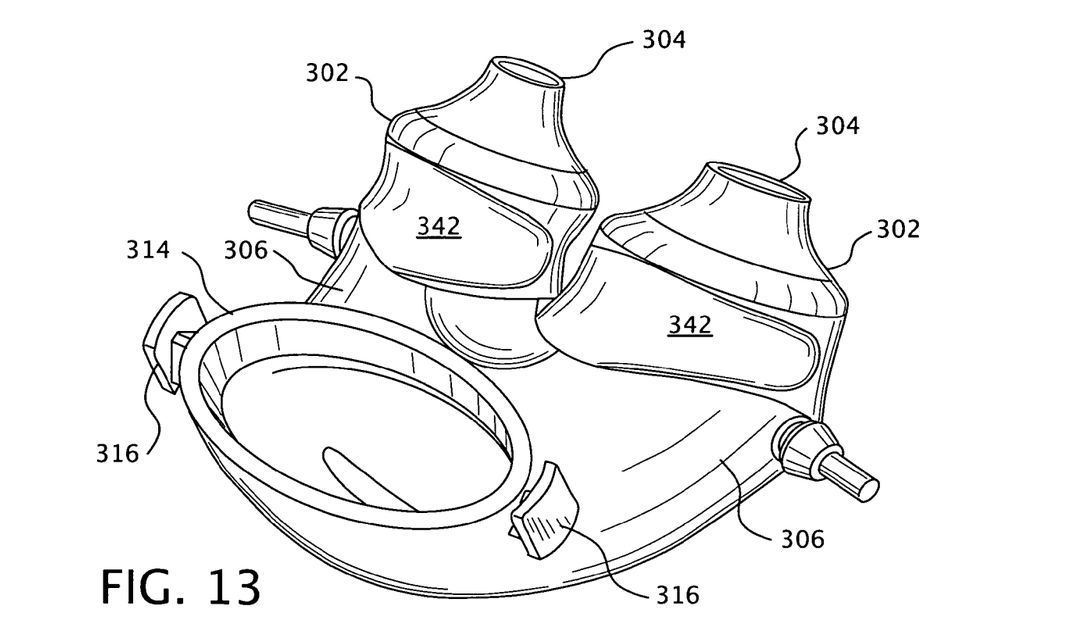
FIG. 13 is a rear perspective view of the second alternative embodiment of the cushion.
Figure 14:
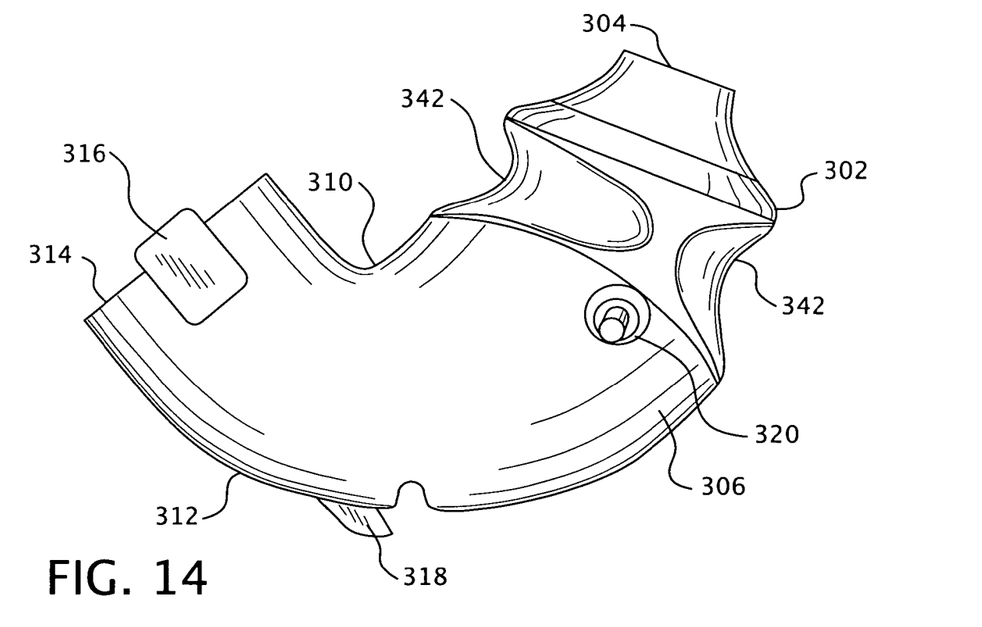
FIG. 14 is a side elevational view of the second alternative embodiment of the cushion.
Figure 15:
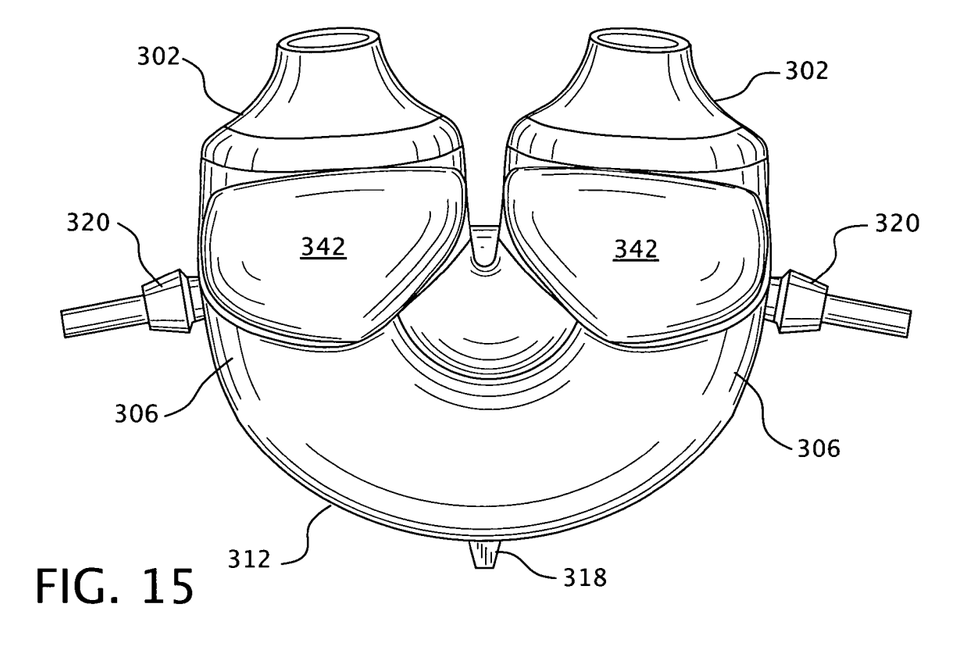
FIG. 15 is a front elevational view of the second alternative embodiment of the cushion.
Figure 17:
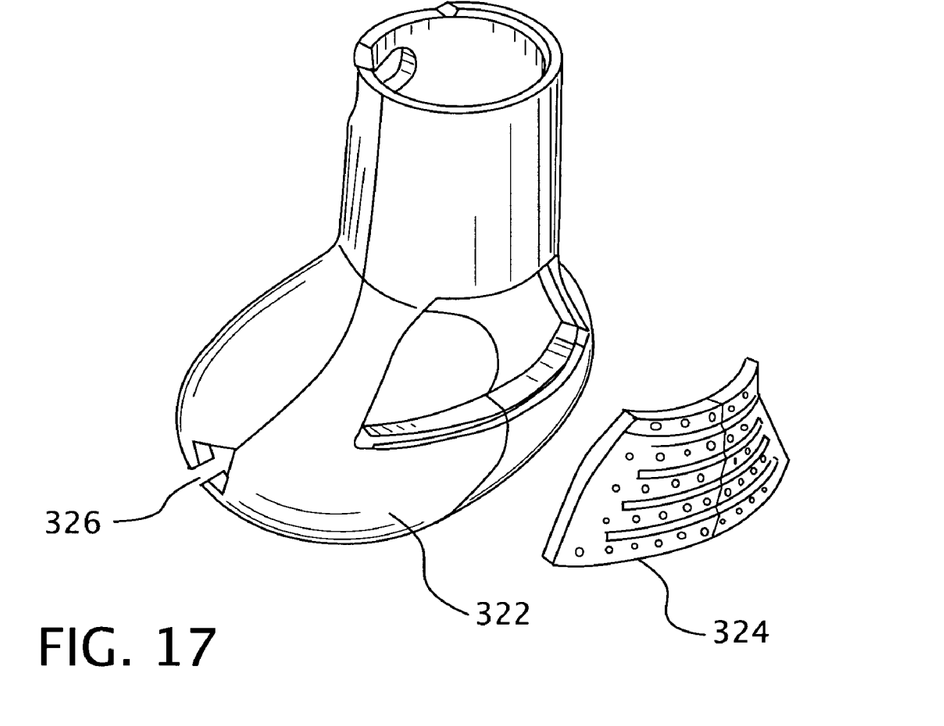
FIG. 17 is a rear perspective view of a coupling of the second alternative embodiment of the cushion.
Figure 18:
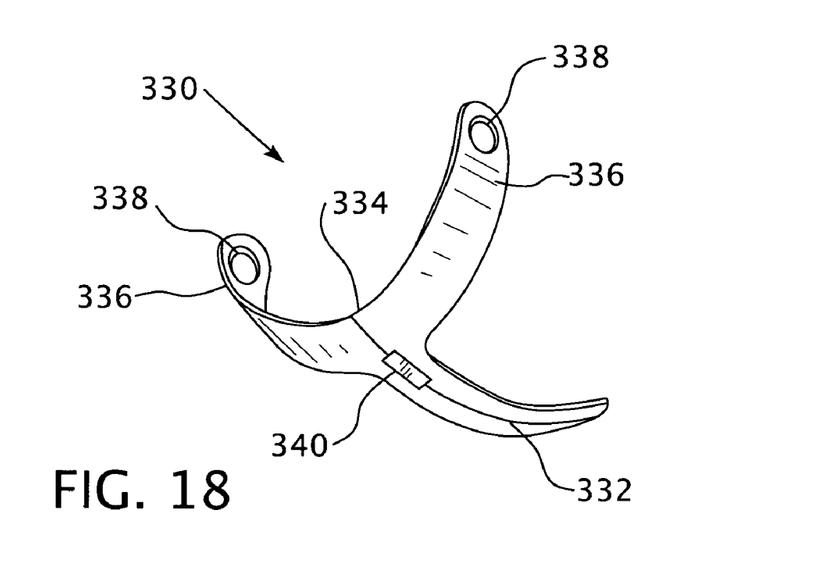
FIG. 18 is a bottom perspective view of a deformable support of the second alternative embodiment of the cushion.

As best appreciated with reference to FIGS. 13 and 14, the body also includes alignment rails 316, alignment fin 318, and bosses or mounting tabs 320. With reference to FIGS. 17 and 18, the cushion is connected to coupling 322. The coupling has a rear exhaust plate 324 and slots 326. Alignment rails 316 fit into slots 326 to interconnect cushion 300 with coupling 322. The pillow 300 is supported by a deformable support 330. Deformable support 330 includes a stem portion 332 and cross portion 334. The stem portion has a slot 340, and the cross portion 334 terminates at ends 336 having holes 338 therethrough. Deformable support 330 is connected to pillow 300 by passing each boss 320 through a corresponding one of the holes 338. In addition, alignment fin is passed through slot 340.

Figure 16:
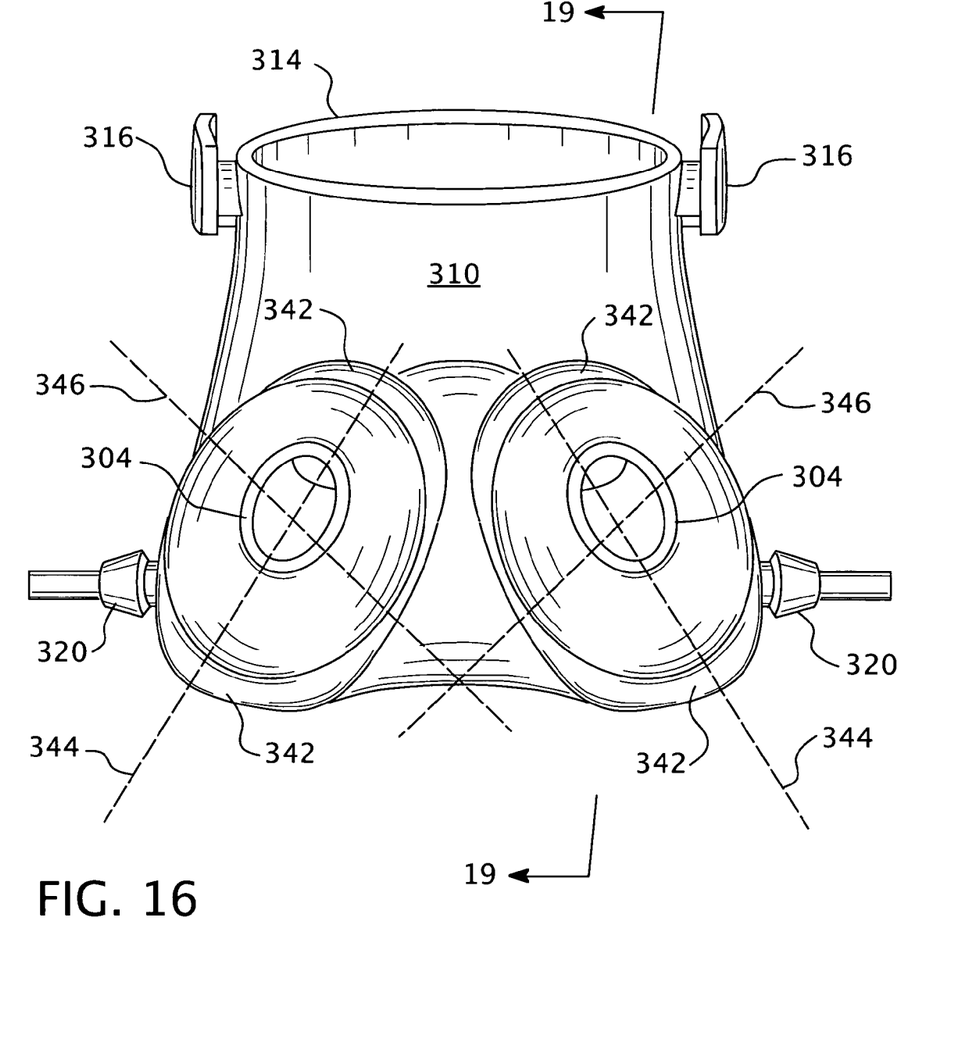
FIG. 16 is a top plan view of the second alternative embodiment of the cushion.

One unique aspect of this embodiment is that each nare element 302 includes at least one pleat 342 that extends around a portion of each nare element 302. As in the prior embodiments, the pleats permit the nare elements 302 to articulate in a controlled manner. For instance, the pleats may be oriented with the region of deepest recess aligned where the most flexibility is desired. As best appreciated with reference to FIG. 16, each nare element has an approximately elliptical cross-section defining a major axis 344 and a minor axis 346 orthogonal to the major axis. Of course, the shape of the nares may have a variety of other shapes without departing from the scope of the present invention. The pleats, in FIG. 16, are oriented such that the region with the deepest recess is approximately aligned with the major axis 344 of each nare element 302 and gradually become shallower towards the minor axis 346. This configuration permits the nare elements 302 to be more flexible and thus pivot along the major axis while simultaneously being relatively more rigid and resist bending along the minor axis 346.

Figure 19:
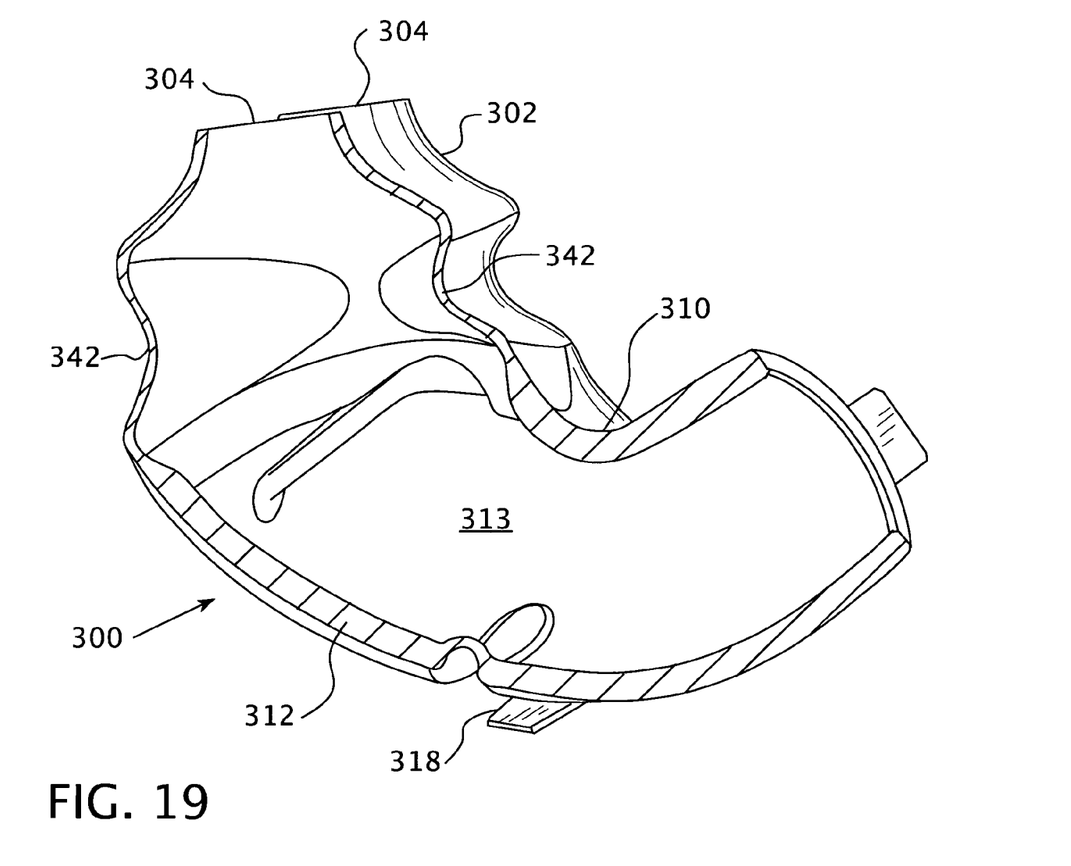
FIG. 19 is a cross-sectional view of the nasal cushion of the second alternative embodiment along line 19-19 of FIG. 16.

With reference to FIG. 19, the nare elements may be further enhanced by forming pleats 342 with a thinner wall thickness in the region of deepest recess. This further permits the nare elements to pivot as well as rotate. The nares may pivot along the major axis and/or rotate about their center in a controlled manner to accommodate the particular nasal configuration of different users. Of course, the pleats may be placed in other locations about the nare elements to promote localized pivoting as deemed desirable without departing from the teachings of the present invention.

One advantageous aspect of this invention is that its unique aspects may be localized in particular regions where their unique characteristics are desirable rather than extending completely about the cushion or pillow. Although the figures disclose a particular configuration, one of ordinary skill in the art can best appreciate that the pleats and wall thickness may be modified to address particular issues in various mask configurations such as full face masks, nasal masks, nasal-oral masks, or nasal pillows. In the event that a particular region is too rigid in the axial direction, the wall thickness could be varied, the depth of the flap could be varied, and/or a pleat could be added. In the event that a particular region, experiences increased radial forces, the wall thickness could be increased, the length of the flaps could be decreased, and/or pleats could be added.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. In addition, specific features of this invention are shown in some drawings and not others, this is for convenience only as each feature may be combined with any or all of the other features in accordance with the invention. Other embodiments will occur to those skilled in the art and are within the following claims:

What is claimed is:

1. A cushion for use in a respiratory mask, the cushion comprises:
    a flap portion;
    a mid portion adjacent the flap portion;
    a connection portion adjacent the mid portion; and
    a pleat formed about a portion of the cushion, wherein the cushion has an apex region, a pair of side regions extending from the apex region, and a bottom region interconnected between the pair of side regions, wherein the pleat extends continuously about the bottom region and at least a portion of the side regions, and wherein the pleat extends discontinuously about the apex region, wherein the apex region includes two apex pleats, wherein each apex pleat is interconnected to the adjacent corresponding side pleat, and wherein the apex pleats are not interconnected to each other.

2. The cushion as recited in claim 1, wherein the flap portion comprises:
    an apex flap having a length;
    a pair of side flaps having a length; and
    a bottom flap having a length.

3. The cushion as recited in claim 2, wherein the length of the apex flap is longer than the length of the bottom flap.

4. The cushion as recited in claim 1, wherein the flap portion has a thickness, the middle portion has a thickness, and the connection portion has a thickness.

5. The cushion as recited in claim 4, wherein the thickness of the flap portion is less than the thickness of the connection portion.

6. A respiratory mask for use in delivering a gas to a user through a conduit, the respiratory mask comprising:
    a shell, the shell having a coupling connected to the conduit; and
    a cushion coupled to the shell, the cushion comprising:
        a flap portion;
        a mid portion adjacent the flap portion;
        a connection portion adjacent the mid portion; and
        a pleat formed about a portion of the cushion proximate the flap portion, wherein the cushion has an apex region, a pair of side regions extending from the apex region, and a bottom region interconnected between the pair of side regions, wherein the pleat extends continuously about the bottom region and the side regions, and wherein the pleat extends discontinuously about the apex region, wherein the apex region includes two apex pleats, wherein each apex pleat is interconnected to the adjacent corresponding side pleat, and wherein the apex pleats are not interconnected to each other.

7. The cushion as recited in claim 6, wherein the flap portion comprises:
    an apex flap having a length;
    a pair of side flaps having a length; and
    a bottom flap having a length.

8. The cushion as recited in claim 7, wherein the length of the apex flap is longer than the length of the bottom flap.

9. The cushion as recited in claim 6, wherein the flap portion has a thickness, the middle portion has a thickness, and the connection portion has a thickness.

10. The cushion as recited in claim 9, wherein the thickness of the flap portion is less than the thickness of the connection portion.

* * * * *